United States Patent [19]

Meilland

[11] Patent Number: Plant 7,390

[45] Date of Patent: Dec. 11, 1990

[54] ROSE PLANT—MEIROLOUR VARIETY

[75] Inventor: Alain A. Meilland, Antibes, France

[73] Assignee: The Conard-Pyle Company, West Grove, Pa.

[21] Appl. No.: 354,284

[22] Filed: May 19, 1989

[30] Foreign Application Priority Data

Oct. 17, 1988 [FR] France ..... 8037

[51] Int. Cl.[5] ..... A01H 5/00

[52] U.S. Cl. ..... Plt./20

[58] Field of Search ..... Plt. 20

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which forms in abundance attractive fully double blossoms which exhibit a long vase life. The blossoms are currant red on the upper surface and light cardinal red on the lower surface. The plant exhibits an erect growth habit, vigorous vegetation, and is well adapted for cut flower production in a greenhouse. Good resistance to fungal diseases also in manifest.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Jacqueline variety (U.S. Plant Pat. No. 2,183). The male parent (i.e., the pollen parent) of the new variety was the Samantha variety (U.S. Plant Pat. No. 3,727). The parentage of the new variety can be summarized as follows:

Jacqueline × Samantha.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long lasting fully double blossoms which are currant red on the upper surface and light cardinal red on the lower surface,
(b) exhibits an erect growth habit,
(c) forms vigorous vegetation,
(d) is well adapted to greenhouse forcing for cut flower production, and
(e) exhibits good resistance to cryptogamic diseases.

The new variety is totally different than its Jacqueline parent in the shape of the bud and in the blossom coloration. More specifically, the blossoms of the Jacqueline parent possess an orange-red coloration rather than the dark red coloration of the present variety.

The new variety differs from the Samantha parent in a number of significant areas. More specifically, the new variety tends to exhibit more dense foliage, larger leaflets, a bud configuration having a lesser width, a slightly different blossom coloration, and somewhat shorter stems.

No hips have been observed on the new variety to date whether grown in a greenhouse or in the field.

The new variety well meets the needs of the horticultural and is particularly well-suited for the production of cut flowers.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meirolour variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while grafted on *Rosa indica* understock and growing in greenhouse at Cap d'Antibes, France.

DETAILED DESCRIPTION

Figures 1, 2, 3, 4, 5, 6, 7, 8, 9, 10, 11, 12, 13, 14, 15, 16, 17:
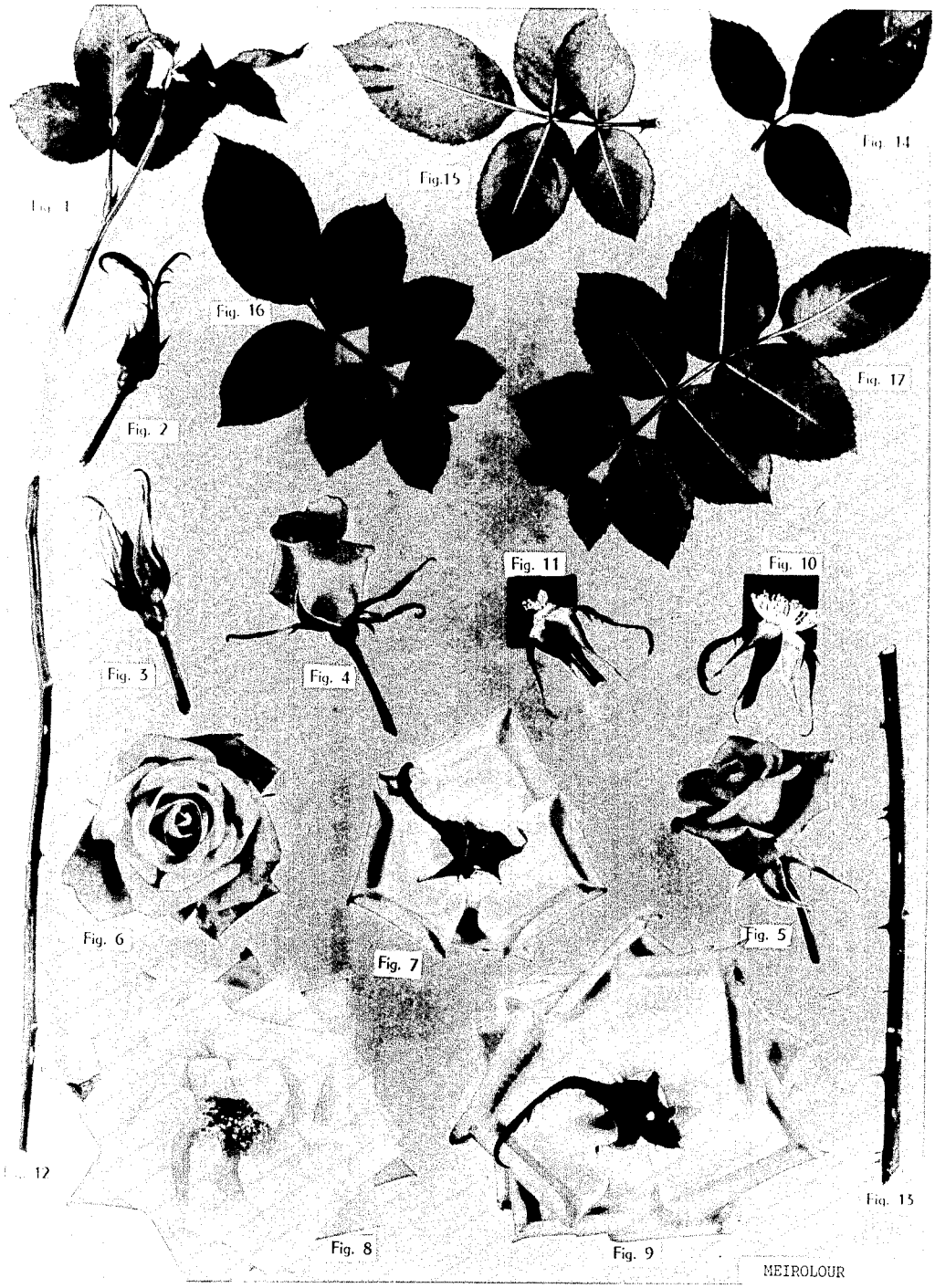
FIG. 1 illustrates a specimen of a young shoot.
FIG. 2 illustrates a specimen of a floral bud before the opening of the sepals.
FIG. 3 illustrates a specimen of a floral bud when the sepals open.
FIG. 4 illustrates a specimen of a floral bud when the petals open.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.
FIG. 17 illustrates a specimen of a leaf with nine leaflets — plan view — under surface.

The chart used in the identification of the colors is that of The Royal Horticultural Society (R.H.S. Colour Chart). The description is based on observations of two year old specimens made during November while grafted on *Rosa indica* understock and growing in greenhouses at Cap d'Antibes, France. Color terminology in common terms precedes the reference to such chart.

Class: Hybrid Tea.

Plant:

*Height.*—Plants which were pruned to a height of 85 cm. commonly produce floral stems having a length of approximately 40 to 60 cm.

*Habit.*—Erect.

Branches:

Color.—Young stems: light green, Green Group 143B. Adult wood: medium green, Green Group 143A.

*Thorns.*—Size: small. Quantity: few. Color: greenish on young stems and greenish changing to tan on mature wood.

Leaves:

Stipules.—Adnate, pectinate, wide and linear.

*Petioles.*—Upper surface: striped, reddish brown on young foliage and medium green on adult foliage with more or less glandular edges. Under surface: light green and smooth.

Leaflets.—Number 3, 5 (most often), 7, and sometimes 9. Sometimes the first leaflet pair is incomplete. Shape: elliptic. Serration: single and regular. Texture: consistent. General appearance: dense and semi-dull foliage. Color (young foliage): Upper surface: reddish brown. Under surface: reddish brown. Color (adult foliage): Upper surface: dark green, Green Group 143A. Under surface: light green, Green Group 138B.

Inflorescence:

*Number of flowers.*—Generally one per stem.

*Peduncle.*—Straight, rigid, smooth and light green in coloration, approximately 10 to 11 cm. in length on average.

*Sepals.*—Upper surface: tomentose and greenish in coloration. Under surface: light green in coloration, the outside sepals are slightly appendiculated.

*Buds.*—Shape: conical. Length: approximately 3 cm. on average. Size: large. Color upon opening: Upper surface: currant red, Red Group 46A. Under surface: light cardinal red, Red Group 53C.

*Flower.*—Shape: cuplike. Diameter: approximately 11 to 11.5 cm. on average. Color (when opening begins): Upper surface: currant red, Red Group 46A. Under surface: cardinal red, Red Group 53C. Color (when blooming): Upper surface: currant red, Red Group 46A. Under surface: light cardinal red, Red Group 53C. Color (at end of opening): Upper surface: currant red, Red Group 46A. Under surface: cardinal red, Red Group 53C. Fragrance: none. Lasting quality: long. Petal number: approximately 29 to 37 on average. Texture: consistent. Petal drop: good. Stamen number: approximately 63 to 68 on average. Anthers: normal, yellowish in coloration. Filaments: yellowish at base with fuschia tips, of irregular heights. Pistils: approximately 61 to 66 on average. Stigmas: normal, straw yellow in coloration. Styles: dark fuschia in coloration, more or less twisted, tomentose at base, of irregular heights. Receptacle: medium green in coloration, smooth, and in longitudinal section in the shape of a wide pitcher.

Development:

*Vegetation.*—Vigorous.

*Blooming.*—Very floriferous.

*Aptitude to forcing.*—Excellent.

*Resistance to disease.*—Good.

I claim:

1. A new and distinct variety of Hybrid Tea rose plant characterized by the following combination of characteristics:

(a) forms in abundance attractive long lasting fully double blossoms which are currant red on the upper surface and light cardinal red on the lower surface, (b) exhibits an erect growth habit, (c) forms vigorous vegetation, (d) is well adapted to greenhouse forcing for cut flower production, and (e) exhibits good resistance to cryptogamic diseases;

substantially as herein shown and described.

* * * * *

MEIROLOUR